US006191365B1

(12) United States Patent
Avellanet

(10) Patent No.: US 6,191,365 B1
(45) Date of Patent: *Feb. 20, 2001

(54) MEDICAL DEVICES INCORPORATING AT LEAST ONE ELEMENT MADE FROM A PLURALITY OF TWISTED AND DRAWN WIRES

(75) Inventor: Francisco J. Avellanet, Coral Gables, FL (US)

(73) Assignee: General Science and Technology Corp, MIami, FL (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 51 days.

This patent is subject to a terminal disclaimer.

(21) Appl. No.: 09/143,984

(22) Filed: Aug. 31, 1998

Related U.S. Application Data

(63) Continuation-in-part of application No. 09/060,969, filed on Apr. 15, 1998, now Pat. No. 6,137,060, and a continuation-in-part of application No. 09/087,476, filed on May 29, 1998, now abandoned, and a continuation-in-part of application No. 09/044,203, filed on Mar. 17, 1998, and a continuation-in-part of application No. 08/843,405, filed on May 2, 1997, now Pat. No. 5,994,647, and a continuation-in-part of application No. 08/963,686, filed on Nov. 4, 1997, now Pat. No. 6,049,142, and a continuation-in-part of application No. PCT/US97/18057, filed on Oct. 7, 1997.

(51) Int. Cl.[7] .................................................. H01B 5/10
(52) U.S. Cl. ............................................. 174/128.1
(58) Field of Search ........................... 174/128.1, 128.2, 174/126.1, 125.1

(56) References Cited

U.S. PATENT DOCUMENTS

| | | | |
|---|---|---|---|
| 3,131,469 | * 5/1964 | Glaze ............................ | 174/128.1 X |
| 3,261,908 | * 7/1966 | Roche et al. ................... | 174/128.1 |
| 3,620,212 | 11/1971 | Fannon, Jr. ..................... | 128/130 |
| 4,027,677 | 6/1977 | Schulman et al. ............... | 128/418 |
| 4,037,324 | 7/1977 | Andreasen ...................... | 32/14 |
| 4,215,703 | 8/1980 | Willson .......................... | 128/772 |
| 4,233,690 | 11/1980 | Akins ............................. | 3/1.5 |
| 4,493,320 | 1/1985 | Treat .............................. | 128/303.15 |
| 4,665,906 | 5/1987 | Jervis ............................. | 128/92 YN |
| 4,830,003 | 5/1989 | Wolff ............................. | 128/343 |
| 4,830,262 | 5/1989 | Ishibe ............................. | 228/156 |
| 4,925,445 | 5/1990 | Sakamoto et al. ............... | 604/95 |
| 5,064,428 | 11/1991 | Cope et al. ..................... | 606/127 |
| 5,067,957 | 11/1991 | Jervis ............................. | 606/108 |
| 5,112,136 | 5/1992 | Sakuma et al. ................. | 374/44 |
| 5,118,906 | * 6/1992 | Kudoh et al. ................... | 174/128.1 X |
| 5,146,928 | 9/1992 | Esser .............................. | 128/756 |
| 5,201,323 | 4/1993 | Vermeulen ..................... | 128/756 |
| 5,201,741 | 4/1993 | Dulebohn ....................... | 606/113 |
| 5,213,111 | 5/1993 | Cook et al. ..................... | 128/772 |
| 5,230,348 | 7/1993 | Ishibe et al. .................... | 128/772 |
| 5,263,964 | 11/1993 | Purdy ............................. | 606/200 |
| 5,282,824 | 2/1994 | Gianturco ....................... | 606/198 |
| 5,292,331 | 3/1994 | Boneau ........................... | 606/198 |
| 5,322,508 | 6/1994 | Viera .............................. | 604/52 |
| 5,376,100 | 12/1994 | Lefebvre ......................... | 606/180 |
| 5,395,386 | 3/1995 | Slater ............................. | 606/170 |
| 5,423,829 | 6/1995 | Pham et al. .................... | 606/108 |
| 5,429,139 | 7/1995 | Sauter ............................ | 128/772 |
| 5,439,000 | 8/1995 | Gunderson et al. ............. | 128/664 |
| 5,482,054 | 1/1996 | Slater et al. .................... | 128/751 |
| 5,483,022 | * 1/1996 | Mar ............................... | 174/128.1 X |
| 5,496,330 | 3/1996 | Bates et al. ..................... | 606/127 |
| 5,507,296 | 4/1996 | Bales et al. ..................... | 128/751 |
| 5,520,194 | 5/1996 | Miyata et al. .................. | 128/772 |
| 5,549,606 | 8/1996 | McBrayer et al. .............. | 606/51 |
| 5,549,635 | 8/1996 | Solar .............................. | 606/198 |
| 5,562,697 | 10/1996 | Christiansen ................... | 606/191 |
| 5,569,244 | 10/1996 | Hahnen .......................... | 606/46 |
| 5,597,378 | 1/1997 | Jervis ............................. | 606/78 |
| 5,601,600 | 2/1997 | Ton ................................ | 606/206 |
| 5,639,277 | 6/1997 | Mariant et al. ................. | 606/191 |
| 5,667,525 | 9/1997 | Ishibashi ........................ | 606/206 |
| 5,674,278 | 10/1997 | Boneau .......................... | 623/1 |
| 5,718,159 | * 2/1998 | Thompson ...................... | 87/33 |

FOREIGN PATENT DOCUMENTS

| | | |
|---|---|---|
| 0 480427A1 | 10/1991 | (EP) . |
| 0 649636A2 | 9/1994 | (EP) . |
| 197692 | * 5/1923 | (GB) ............................ 174/128.1 X |

OTHER PUBLICATIONS

Hesterlee, Jerry M., "Trapwire Constructions," Wire Technology International, pp. 51–52, Mar. 1997.*

* cited by examiner

Primary Examiner—Dean A. Reichard
(74) Attorney, Agent, or Firm—David P. Gordon; David S. Jacobson; Thomas A Gallagher

(57) ABSTRACT

Medical devices are provided which utilize a highly flexible cable of two and preferably three or more strands of wire. The strands are twined to form a wire rope which is drawn through successive dies to reduce its diameter until the outer surface of the cable is substantially smooth. A cable so-formed has improved elasticity. The cable is used in medical devices in which increased elasticity of a wire-like element is desired. Twisted and drawn cables incorporating a strand of a radiopaque metal or alloy may be used in devices in which radiopacity of a flexible portion of the device is desired. Twisted and drawn cables incorporating a strand of a metal or alloy having high electrical conductance may be used in devices in which electrical conductivity of a flexible portion of the device is desired.

33 Claims, No Drawings

MEDICAL DEVICES INCORPORATING AT LEAST ONE ELEMENT MADE FROM A PLURALITY OF TWISTED AND DRAWN WIRES

This application is a continuation-in-part of U.S. Ser. No. 09/060,969 filed Apr. 15, 1998 U.S. Pat. No. 6,137,060, a continuation-in-part of U.S. Ser. No. 09/087,476 filed on May 29, 1998 now abandoned, a continuation-in-part of U.S. Ser. No. 09/044,203 filed on Mar. 17, 1998, a continuation-in-part of U.S. Ser. No. 08/843,405 filed May 2, 1997 U.S. Pat. No. 5,994,647, a continuation-in-part of U.S. Ser. No. 08/963,686 filed Nov. 4, 1997 now U.S. Pat. No. 6,049,042, and a continuation-in-part of PCT/US97/18057 filed Oct. 7, 1997 and claiming priority from U.S. Ser. Nos. 08/730,489 filed Oct. 11, 1996, 08/856,571 filed May 15, 1997, and 08/554,336 filed Nov. 6, 1995, all of which are hereby incorporated by reference herein in their entireties.

BACKGROUND OF THE INVENTION

1. Field of the Invention

This invention relates broadly to medical devices incorporating elements having a low modulus of elasticity. More particularly, this invention relates to medical devices incorporating one or more cable elements made from a plurality of twisted and drawn wires.

2. State of the Art

Wires are utilized throughout the medical arts. In many medical devices a particularly desirable feature for the wires is high elasticity. For example, in baskets and snares high elasticity may be the most important property of the wires used. The elasticity of the wires comprising snares and baskets is a factor in the extent to which each may be compressed for insertion to the surgical site and yet still be able to expand upon use. In addition, higher elasticity permits the baskets and snares to be contracted about smaller radii.

The need for highly flexible self-expanding stents is also well-known. Flexibility not only permits proper stent deployment, but also enables the stent to better conform to the vascular walls.

In endoscopic instruments, a control wire is often coupled between a proximal handle and a distal end effector. The control wire is used to translate movement of the handle into operation of the end effector. The wire must be able to easily bend through the tortuous paths through which endoscopic instruments are guided.

Wire flexibility is also important in numerous other medical devices. For that reason, the medical arts have recently had much interest in nickel-titanium alloy (Nitinol) wires which exhibit superelastic characteristics. However, Nitinol is relatively expensive, and alternatives to Nitinol offering comparable advantage in the medical device arts are desired.

In addition, with respect to many medical devices, the art has gone to great lengths and expense to provide radiopaque materials to the distal end of Nitinol elements (see, e.g., U.S. Pat. No. 5,520,194 to Miyata et al.). This is particularly required in devices using very fine (i.e., small diameter) Nitinol wires which cannot easily be seen during fluoroscopy. However, radiopaque materials are difficult to attach to the Nitinol components owing, in part, to their dissimilarity with the Nitinol material. Moreover, it is preferable in certain applications to have an elastic component which conducts electricity sufficiently to permit cautery functions or to permit the component to function as an electrical lead. However, nickel-titanium alloys are not particularly good conductors.

SUMMARY OF THE INVENTION

It is therefore an object of the invention to provide a variety of medical devices which utilize one or more multifilament twisted and drawn cables that exhibit excellent elasticity characteristics.

It is another object of the invention to provide medical devices with a radiopaque elastic element.

It is also object of the invention to provide medical devices which include a conductive elastic element.

It is a further object of the invention to provide medical devices which include a radiopaque, conductive, and elastic element.

In accord with these objects, which will be discussed in detail below, medical devices are provided which utilize a highly flexible cable of two and preferably three or more strands of wire, which are twined to form a wire rope which is drawn through successive dies to reduce its diameter until the outer surface of the cable is substantially smooth. Where the resulting cable is made from strands of a single material, the cable is provided with improvement elasticity and torqueability over of a wire of the same material having the same diameter as the cable. The cable is used in medical devices in which increased elasticity of a wire-like element is desired at a more reasonable cost than nickel-titanium wires. Twisted and drawn cables incorporating at least one strand of a radiopaque metal or alloy may be used in devices in which radiopacity of an elastic portion of the device is desired. Twisted and drawn cables incorporating at least one strand of a highly electrically conductive metal or alloy may be used in devices in which electrical conductivity of an elastic portion of the device is desired. Twisted and drawn cables incorporating at least one strand of a radiopaque metal or alloy with at least one strand of a highly electrically conductive alloy may be used in devices in which radiopacity of an electrically conductive elastic portion of a device is desired.

Additional objects and advantages of the invention will become apparent to those skilled in the art upon reference to the detailed description.

DETAILED DESCRIPTION OF THE PREFERRED EMBODIMENTS

The invention will be described by first introducing the concept of cables formed from multistrand twisted and drawn wires. Then, examples will be provided illustrating how such cables can be substituted for conventional wires (e.g., stainless steel wires and nickel-titanium alloy wires) in medical devices to achieve the beneficial results of the invention.

The invention is the improvement of a variety of medical devices by utilizing therein a cable of two and preferably three or more strands of wire which are twined to form a wire rope. The wire rope is drawn through successive dies to reduce its diameter until the outer surface of the cable is substantially smooth, the cross section of the cable is substantially circular, and the overall diameter of the wire rope is reduced by 20–50%. The cable is then annealed to remove the effects of cold working.

The resulting cable has been found to have an improved flexibility (i.e., a lower modulus of elasticity) relative to a single wires of the same diameter and same constituent metals or alloys. Moreover, such cables have high torqueability and exhibit strong radial strength.

In addition, a twisted and drawn cable including one or more strands of a radiopaque material, e.g., gold, silver, or platinum-iridium, will exhibit both elastic and radiopaque properties. In accord with the invention, the cable so formed may be used in devices in which radiopacity of a flexible portion of a medical device is desired, e.g., for viewing the flexible portion during fluoroscopic procedures.

Also, a cable including one or more strands having high conductance, e.g., platinum, gold, silver, copper, or aluminum strands, will exhibit desirable elastic and electrical conductance properties. In accord with the invention, the cable so formed may be used in devices in which high electrical conductivity of a flexible portion of a medical device is desired.

Moreover, in accord with the invention, cables incorporating at least one strand of a radiopaque metal or alloy, and at least one strand of an electrically conductive metal may be used in devices in which a radiopaque, conductive, and flexible portion of the device is desired. It will be appreciated that the radiopaque strand and strand having high conductance may be the same strand, e.g., a gold or silver strand.

Furthermore, it will be appreciated that cables may be formed from particular ratios of materials by selecting the number and relative diameter of the wire strands of each material used in the manufacture of the cable. Such ratios permit the selection of varying degrees of elasticity, radiopacity, and conductance according to a particular application.

Particular cables, their manufacture, and their properties are described in detail in previously incorporated co-pending U.S. application Ser. Nos. 08/856,571 to Avellanet et al., 08/843,405 and 08/963,686 to Avellanet, 09/044,203 and 09/087,476 to Avellanet et al., 09/048,746 to Bales et al., and 09/060,969 to Avellanet. From reference to the respective disclosures, it will be appreciated that any particular cable composition described herein may be made by one skilled in the art. The following are examples of uses of twisted and drawn cables in medical devices.

EXAMPLE 1

Surgical Baskets

Baskets are typically used to remove calculi in the form of kidney stones, gallstones and the like from the body without requiring major surgery. Baskets are generally formed from wires defining at least two loops relatively oriented to form a cage-like enclosure. U.S. Pat. No. 5,064,428 to Cope et al. discloses a basket device using a plurality of superelastic wires to form a basket at the distal end of the device, and is hereby incorporated by reference herein in its entirety. U.S. Pat. No. 5,496,330 to Bates et al., which is also hereby incorporated by reference herein in its entirety, discloses another device having a basket comprised of a relatively larger number of shape memory wires for increasing the contact between the basket and entrapped calculi. Other baskets utilize stainless steel wires. However, it is noted by Bates et al. that increasing the number of wires requires the use of wires with relatively smaller diameters. Such smaller diameter wires are weaker and limit the radially acting dilating force that the wires exert against surrounding tissue when the retrieval basket expands, thus making it more difficult to entrap calculi. Furthermore, such baskets are difficult to cannulate through the gallbladder anatomy. Baskets are required to pass smoothly through such areas as the cystic ducts, the common bile duct, and the intestines, as well as being able to retrieve stones from distal sites while causing minimal injury and discomfort to the patient.

By using multistrand twisted and drawn elastic cables in lieu of wires in a basket device, a number of disadvantages in the prior art are overcome. First, baskets comprised of elastic twisted and drawn cables can be easily maneuvered through the tortuous pathways of the anatomical systems in which they are used, as the cable loops forming the basket can be tightly compressed. Second, the cables are more torqueable and can be better steered. Third, smaller diameter cables can be used which have comparable strength to relatively larger wires and which can exert the requisite radial force to maneuver surrounding tissue to facilitate capture and removal of the calculi. Fourth, by using a radiopaque twisted and drawn cable, the baskets are more easily and inexpensively seen under for fluoroscopic viewing during surgical procedures. Fifth, the basket device can be manufactured more economically than a basket using nickel-titanium wires.

It will be further appreciated that in a basket construction, not all of the 'wires' need by twisted and drawn multifilament cables. In fact, by utilizing the twisted and drawn cables in conjunction with more conventional wires, the basket may be provided with portions of relatively higher and lower radial strengths thereby aiding steerability. Similarly, a combination of cables, and preferably also wires, of varying diameters can also provide an increased level of flexibility in a desired direction. Likewise, by using twisted and drawn cables having selected ratios of materials, steerabilty can also be enhanced.

It will also be understood that a basket made of conventional materials may be provided on a multifilament twisted and drawn cable shaft, e.g., a shaft cable comprised of stainless steel twisted and drawn wires, which is joined to the basket at the distal end of the shaft via a sleeve by welding, soldering, or crimping. This arrangement provides higher torqueability than provided with existing stainless steel wire shaft instruments.

EXAMPLE 2

Snares

Snares are used for the endoscopic removal of tissue growths within a body cavity. An exemplar snare device is described in U.S. Pat. No. 5,201,741 to Dulebohn, which is hereby incorporated by reference herein in its entirety. Snare devices generally include an elongate tubular member and an elastic wire (e.g., stainless steel or Nitinol) forming a loop movable distally and proximally within the tubular member to cause the loop to change size. The wire is moved relatively distally to the tubular member to enlarge the loop to surround the tissue, and then relatively proximally to constrict the loop about the growth to excise the growth. The wire may be trained to naturally assume the desired enlarged size. However, a concern with snares is the ability to constrict the loop without plastically deforming the wire about a small radius which would destroy the functionality of the snare.

A twisted and drawn cable made from stainless steel wires provides a snare having a relatively high recoverable elastic strain which permits the snare loop to be constricted about a relatively tight radius. In addition, the twisted and drawn cable has high torqueability and can be better steered around the tissue to be excised.

In addition, it is known to construct snare devices having bipolar cautery capability. See, for example, U.S. Pat. No. 4,493,320 to Treat, which is hereby incorporated by reference herein in its entirety. Such snare devices include an electrically insulated tubular member having two lumina, a pair of flexible electrically conductive snare wires extending from the lumina, an electrically insulating connector for mechanically uniting but electrically insulating the snare wires in a form of a surgical loop extending from one end of the tubular member, and an attachment for electrically connecting the opposite ends of the snare wires to a cautery current source. It will be appreciated that conductive elastic twisted and drawn cables may be used in such a device in place of the known conductive wires to enhance the elasticity of the snare.

EXAMPLE 3

Control Cables for Endoscopic and Laparoscopic Instruments

Endoscopic instruments typically include a proximal actuation handle, a tubular member, one or two control wires, and a distal end effector. The distal end effector may be any of numerous types. For example, U.S. Pat. No. 5,507,296 to Bales et al. discloses a biopsy forceps jaw assembly; U.S. Pat. No. 5,667,525 to Ishibashi discloses a grasping forceps; U.S. Pat. No. 5,395,386 to Slater discloses scissors end effectors; and U.S. Pat. No. 5,549,606 to McBrayer et al. discloses a bipolar grasper end effector. Each of the aforementioned patents is hereby incorporated by reference herein in its entirety for their disclosure of the particular end effector described therein, for the operation of endoscopic instruments in general, and for any other disclosure useful to one skilled in the art. It will be appreciated that other end effectors may alternatively be provided.

The tubular member of the endoscopic instrument, which is often a coil, preferably includes a distally positioned clevis means on which the end effectors are rotatably coupled. The control wire (or wires) extends through the tubular member. The actuation handle includes a stationary member, coupled to the proximal end of either the control wire (or wires) or the tubular member, and a movable member coupled to the proximal end of the other of the control wire (or wires) and the tubular member, such that moving the movable member relative to the stationary member imparts movement of the control wire (or wires) relative to the tubular member to operate the end effector.

The control wire is generally a stainless steel wire. However, as the control wire must be able to easily bend through the tortuous paths through which the endoscopic instrument is guided, control wire flexibility is important. Therefore, in accord with the invention, an elastic twisted and drawn stainless steel cable is used as the control wire.

In addition, U.S. Pat. No. 5,482,054 to Bales, which is hereby incorporated herein in its entirety, discloses a bipolar biopsy forceps. The control wires of the disclosed device may be electrically conductive, elastic twisted and drawn cables, as described above, such that bipolar cautery capability is provided via the control 'cables'.

Similarly, laparoscopic instruments may be provided with one or more control cables in the same manner as the above described endoscopic instruments.

EXAMPLE 4

Rotary Atherectomy (Thrombectomy) Device

U.S. Pat. No. 5,376,100 to Lefebvre, which is hereby incorporated by reference herein in its entirety, discloses an atherectomy or thrombectomy device which comprises a rotary member having flexible filiform elements joined at their distal and proximal ends. When the rotary member is rotated at high speed, the elements are transversely expanded by the effect of the centrifugal force.

The flexible filiform elements and the rotary member may both be comprised of twisted and drawn cables. It will be appreciated that such twisted and drawn cables have excellent flexibility, and is well-adapted for the filiform elements. It will be further appreciated that a twisted and drawn cable has high torqueability, and is well-adapted for the rotary member.

EXAMPLE 5

Stents

Self-expanding stents are generally formed from a spring metal or other resilient material and are deployable through a guiding catheter on a delivery catheter covered with a lubricous sleeve. When the sleeve is withdrawn over the self-expanding stent, the stent automatically expands so as to exert pressure against the surrounding vessel wall. Self-expanding stents are disclosed in, e.g., U.S. Pat. Nos. 4,580,568 to Gianturco; 4,830,003 to Wolff et al.; 5,549,635 to Solar; 5,562,697 to Christiansen; and 5,292,331 and 5,674,278 to Boneau, which are all hereby incorporated by reference herein in their entireties. Such stents are typically formed from a single small diameter wire having a multiplicity of back and forth bends in a zig-zag or sinusoidal path to form an elongate self-expanding structure, or a plurality of self-expanding segments coupled by links, each of the segments defined by a wire having a zig-zag or sinusoidal path, or a plurality of plaited wires.

Self-expanding stents need to be flexible. Such flexibility determines the ease of which the stents may be maneuvered through the curves of blood vessels to the lesion site. In accord with the invention, a stent device is comprised of one or more twisted and drawn cables, preferably comprised of stainless steel wires, and more preferably including at least one radiopaque strand. The enhanced flexibility of a stent device thus comprised facilitates insertion of the stent device to its deployment location. Also, the radiopaque elastic cable of the stent enables improved fluoroscopic viewing of the stent device within the human body to ensure that the device is properly positioned and further to ensure that the device is functioning properly.

EXAMPLE 6

Resection Electrodes

Electrosurgical resection is a procedure in which damaged or enlarged tissue is excised with an electrocautery probe. U.S. Pat. No. 5,569,244 to Hahnen discloses an electrocautery probe, and is hereby incorporated by reference herein in its entirety. The electrocautery probe has a distal resection electrode which is mounted between a pair of arms. The arms are joined at their proximal ends to an electrode lead which is coupled via a handle to a source of cautery current. The electrodes are generally made from cobalt chromium or carbonless stainless steel.

The resection procedure involves applying a cauterizing voltage to the electrode and moving the electrode slowly through or over a tissue. Thermal energy is applied through the electrode, and the tissue in contact is excised. The resectoscope and cautery probe are also useful in procedures for resecting the prostate, endometrium, uterus, ureter, or renal pelvis.

The resection electrodes of the art are replaced with resection electrodes comprised of a multistrand twisted and drawn cable. The strands comprising the cable preferably include strands of one or more of stainless steel, nickel-chromium, platinum-iridium, and tungsten. The cable may be trained according to methods well-known in the art, to take various shapes, e.g., curved and angular, which facilitate cutting through and cautery of the tissue being resected.

EXAMPLE 7

Embolization Coils

Metallic microcoils are used to bridge (embolize) aneurysms in cerebral arteries. The procedure for deploying the coil involves the use of a microcatheter which is delivered through the vasculature to the site of the aneurysm. When the catheter is in place, a stainless steel wire with a platinum coil soldered or otherwise coupled to its distal end is fed through the catheter to the site of the aneurysm. The coil is separated from the wire by the application of a small current which causes the solder to melt, or by mechanical means. Embolization coils are described in U.S. Pat. Nos. 5,263,964 to Purdy, 5,639,277 to Mariant et al., 5,601,600 to Ton, 5,423,829 to Pham et al., and 5,122,136 to Guglielmi et al., which are all hereby incorporated by reference herein in their entireties.

According to the invention, the delivery wire and/or the coil is comprised of a multifilament twisted and drawn cable. Preferably, the cable comprising the coil includes at least one strand of platinum or other radiopaque material.

EXAMPLE 8

Myocardial Leads

The use of myocardial leads is well-known, in either bipolar or monopolar configurations, to stimulate the surface of a heart by the application of electrical pulses. U.S. Pat. No. 4,027,677 to Schulman, which is hereby incorporated by reference herein in its entirety, discloses the art of pacer leads in general. Typically, a myocardial lead consists of an electrode having a pin extending therefrom. The pin is inserted and secured in the myocardium and electrical pulses are supplied to the electrode from an appropriate source, such as a pacemaker, via a wire connected between the electrode and the pacemaker. The electrode is generally in the form of a bent platinum rod, one end of which serves as the electrode pin. Platinum, while biocompatible and able to pass electrical currents either anodically or cathodically into a saline solution, such as the solution present in the body, without corrosion, tends to break quite easily under the stress of heart motion and body movement.

The improved electrode of the invention comprises a twisted and drawn multifilament cable including one or more highly electrically conductive strands. Preferably the conductive strands (or strands) are made from platinum. More preferably, the cable is constructed from platinum and stainless steel. In accord with the invention, the stainless steel strand (or strands) may be surrounded by the platinum strands to inhibit corrosion, e.g., in a five strand about one strand configuration. Alternatively, the stainless steel strands may surround the one or more platinum strand. As yet another alternative, the strands of stainless steel and platinum may be intertwined. The resulting cable is able to pass current, resist corrosion, and is more elastic than pure platinum wires.

EXAMPLE 9

Orthodontic Cables

U.S. Pat. No. 4,037,324 to Andreasen, the disclosure of which is hereby incorporated by reference herein in its entirety, discloses the use of dental wires made of nickel-titanium alloys instead of conventional 18-8 stainless steel wires. The Andreasen reference discloses the advantage of using wires which have a lower elastic modulus and higher elastic limit than stainless steel. In accord with the invention, multifilament twisted and drawn cables made from stainless steel strands provide an orthodontic cable having a lower elastic modulus and higher elastic limit than stainless steel orthodontic wires and a significantly lower cost than nickel-titanium wires.

EXAMPLE 10

Heart Valves

U.S. Pat. No. 4,233,690 to Akins, the disclosure of which is hereby incorporated by reference herein in its entirety, discloses the use of a conventional shape memory alloy ring to hold a sewing cuff to the body of an artificial heart valve. The ring is replaced with a twisted and drawn cable, e.g., made from stainless steel. The resulting ring provides the desired elasticity at a cost more economical than the nickel-titanium constructs.

EXAMPLE 11

IUDs

U.S. Pat. No. 3,620,212 to Fannon et al., the disclosure of which is hereby incorporated by reference herein in its entirety, discloses an intrauterine contraceptive device (IUD) proposed to be formed from a shape memory alloy. In accord with the invention, the IUD is formed from a twisted and drawn cable.

EXAMPLE 12

Cytology Brushes

In some cases, obtaining a forceps biopsy may be difficult. In these cases, the practitioner may obtain cellular samples by brushing with a cytology brush. The cytology brush generally comprises an elongate shaft for extension through an endoscope and a plurality of typically helically arranged bristles at the distal end of the shaft. Exemplar cytology brushes are described in U.S. Pat. Nos. 5,146,928 to Esser and 5,201,323 to Vermeulen, which are hereby incorporated by reference herein in their entireties. In accord with the invention, either or both of the bristles of the brush and the shaft may be comprised of twisted and drawn cable. Bristles of a cable structure are more flexible than the presently-provided bristles, and a twisted and drawn cable shaft is more torqueable than present shafts.

There have been described and illustrated herein a number of medical devices which are improved by utilizing one or more twisted and drawn cable elements in place of elements otherwise constructed. While particular devices and embodiments of the invention have been described (with reference to U.S. patents incorporated herein), it is not intended that the devices be limited to the embodiments disclosed in the incorporated references, only that such references provide the broad teaching of the respective devices. Particularly, each device in the incorporating reference should be read as a representative for all devices of the type of such device and the scope of the invention should be interpreted in this light. In addition, it is clear that other medical devices can be provided which utilize the superelastic cable of the invention. For example, papillotomy knives, surgical staples, braiding elements in catheters, braiding elements for tubes for blood pumps and peristaltic pumps, and other medical devices may incorporate the described cable in accord with the contemplated scope of the invention. Moreover, it will be appreciated that the invention may be utilized in both reusable and disposable instruments. It will therefore be appreciated by those skilled in the art that yet other medical devices could provided with the twisted and drawn cable without deviating from the spirit and scope of the invention as so claimed.

What is claimed is:

1. In a medical device for temporary or permanent insertion or implantation into a human body, the improvement comprising:
   at least one element comprising at least two wires twisted and drawn through at least one die to form a flexible cable.
2. The improvement according to claim 1, wherein:
   said at least two twisted wires comprises at least three wires.
3. The improvement according to claim 1, wherein:
   said at least two twisted wires includes at least one wire which has greater radiopacity than another of said at least two twisted wires.
4. The improvement according to claim 1, wherein:
   said at least two twisted wires comprises at least three stainless steel wires.
5. The improvement according to claim 1, wherein:
   said at least two twisted wires includes at least one wire comprised of at least one of platinum, gold, silver, copper, and aluminum.
6. The improvement according to claim 1, wherein:
   said at least two twisted wires include at least one wire comprised of at least one nickel-chromium, platinum-iridium, and tungsten.
7. The improvement according to claim 1, wherein:
   said at least two twisted wires includes at least one wire made from a first material and at least one wire made from a conductive material having greater conductance than said first material.
8. The improvement according to claim 1, wherein:
   said at least one element includes at least one of a first element comprised of at least two wires twisted and drawn through at least one die, and at least one of a second element comprised of at least two wires twisted and drawn through at least one die, said first element being comprised of a material which is present in said first element in a first ratio, and said second element having said material in a second ratio different than said first ratio.
9. The improvement according to claim 1, wherein:
   said medical device is an endoscopic instrument.
10. The improvement according to claim 9, wherein:
    said at least one element is a control cable in said endoscopic instrument.
11. The improvement according to claim 1, wherein:
    said medical device is a surgical basket device having a basket, and said at least one element is a component of said basket.
12. The improvement according to claim 11, wherein:
    said basket is comprised of said at least one element and at least one wire.
13. The improvement according to claim 11, wherein:
    said at least one element includes at least one of a first element comprised of at least two wires twisted and drawn through at least one of a second element comprised of at least two wires twisted and drawn through at least one die, said second element being comprised of at least one material which is not present in said first element.
14. The improvement according to claim 11, wherein:
    said at least one element includes at least one of a first element comprised of at least two wires twisted and drawn through at least one die, and at least one of a second element comprised of at least two wires twisted and drawn through at least one die, said first element being comprised of a material which is present in said first element in a first ratio, and said second element having said material in a second ratio different than said first ratio.
15. The improvement according to claim 1, wherein:
    said medical device is a surgical snare device, and said at least one element comprises a snare.
16. The improvement according to claim 15, wherein:
    said snare is a bipolar snare.
17. The improvement according to claim 1, wherein:
    said medical device is a rotary atherectomy device.
18. The improvement according to claim 17, wherein:
    said at least one element comprises a rotary member.
19. The improvement according to claim 17, wherein:
    said at least one element comprises a plurality of elements, each of said plurality of elements being a filiform element.
20. The improvement according to claim 1, wherein:
    said medical device is a self-expanding stent.
21. The improvement according to claim 1, wherein:
    said medical device is an electrocautery probe.
22. The improvement according to claim 21, wherein:
    said at least one element is an electrode of said electrocautery probe.
23. The improvement according to claim 1, wherein:
    said medical device is an embolization coil.
24. The improvement according to claim 1, wherein:
    said medical device is a myocardial lead.
25. The improvement according to claim 24, wherein:
    said at least one element is an electrode of said myocardial lead.
26. The improvement according to claim 1, wherein:
    said medical device is an orthodontic cable.
27. The improvement according to claim 1, wherein:
    said medical device is a heart valve.
28. The improvement according to claim 27, wherein:
    said at least one element is a ring component of said heart valve.
29. The improvement according to claim 1, wherein:
    said medical device is an IUD.
30. The improvement according to claim 1, wherein:
    said medical device is a cytology brush.
31. The improvement according to claim 30, wherein:
    said at least one element comprises a plurality of elements, each of said plurality of elements being a bristle of said cytology brush.
32. The improvement according to claim 30, wherein:
    said at least one element is a shaft of said cytology brush.
33. The improvement according to claim 1, wherein:
    said at least two wires are twisted and drawn through said at least one die without brazing to form said flexible cable.

* * * * *

UNITED STATES PATENT AND TRADEMARK OFFICE
CERTIFICATE OF CORRECTION

PATENT NO. : 6,191,365 B1
DATED : February 20, 2001
INVENTOR(S) : Francisco J. Avellanet It is certified that error appears in the above-identified patent and that said Letters Patent is hereby corrected as shown below:

<u>ON THE TITLE PAGE</u>

Item [63] Related U.S. Application Data should read --

Pat. No. 6,049,042 --.

Signed and Sealed this

Twenty-ninth Day of May, 2001

*Attest:*

NICHOLAS P. GODICI

*Attesting Officer*     *Acting Director of the United States Patent and Trademark Office*